United States Patent [19]

Nakama et al.

[11] Patent Number: 4,919,846

[45] Date of Patent: Apr. 24, 1990

[54] DETERGENT COMPOSITION CONTAINING A QUATERNARY AMMONIUM CATIONIC SURFACTANT AND A CARBOXYLATE ANIONIC SURFACTANT

[75] Inventors: Yasunari Nakama; Fuminori Harusawa; Kyoko Otsubo; Tsunehiko Iwai; Shuya Tamaki; Masahiro Ohkoshi, all of Yokohama, Japan

[73] Assignee: Shiseido Company Ltd., Tokyo, Japan

[21] Appl. No.: 249,047

[22] Filed: Sep. 23, 1988

Related U.S. Application Data

[63] Continuation-in-part of Ser. No. 54,342, May 26, 1987, abandoned.

[30] Foreign Application Priority Data

| May 27, 1986 | [JP] | Japan | 61-121962 |
| Sep. 24, 1987 | [JP] | Japan | 62-239717 |
| Nov. 19, 1987 | [JP] | Japan | 62-292933 |
| Nov. 30, 1987 | [JP] | Japan | 62-302791 |
| Nov. 30, 1987 | [JP] | Japan | 62-302792 |

[51] Int. Cl.$^5$ ............... C11D 1/10; C11D 1/65
[52] U.S. Cl. ............... 252/542; 252/117; 252/546; 252/547; 252/DIG. 14; 252/545
[58] Field of Search ....... 252/106, 547, 546, DIG. 14, 252/117, 545

[56] References Cited

U.S. PATENT DOCUMENTS

| 2,950,255 | 8/1960 | Goff | 252/547 |
| 3,553,141 | 1/1971 | Katsumi et al. | 252/106 |
| 3,755,559 | 8/1973 | Hewitt | 424/70 |
| 3,990,991 | 11/1976 | Gerstein | 252/542 |
| 4,061,602 | 12/1977 | Oberstar | 252/547 |
| 4,247,538 | 1/1981 | Barker | 424/70 |
| 4,452,732 | 6/1984 | Bolich | 252/547 |
| 4,486,328 | 12/1984 | Knott et al. | 252/117 |
| 4,576,729 | 3/1986 | Paszek et al. | 252/106 |
| 4,578,216 | 3/1986 | Fujii et al. | 252/542 |
| 4,663,069 | 5/1987 | Llenado | 252/117 |
| 4,725,377 | 2/1988 | Choi | 252/174.19 |

FOREIGN PATENT DOCUMENTS

| 0151936 | 8/1985 | European Pat. Off. |
| 2341592 | 2/1975 | Fed. Rep. of Germany |
| 2641053 | 3/1977 | Fed. Rep. of Germany |
| 2233981 | 1/1975 | France |
| 60706 | 8/1973 | Japan |
| 31707 | 3/1976 | Japan |
| 144099 | 11/1980 | Japan |
| 12000 | 2/1981 | Japan |
| 202391 | 12/1982 | Japan |
| 195200 | 10/1985 | Japan |
| 4799 | 1/1986 | Japan |
| 830880 | 3/1960 | United Kingdom |

OTHER PUBLICATIONS

Esposito et al, "Shampoo–Documentary/Formulary, Cosmetics & Toiletries", vol. 96, Jul. 1981, pp. 99, 100, 101.

Primary Examiner—Prince E. Willis
Attorney, Agent, or Firm—Sprung Horn Kramer & Woods

[57] ABSTRACT

A detergent composition having an excellent conditioning effect and low skin irritation, which contains, in an aqueous medium, (i) at least one quaternary ammonium cationic surfactant selected from the group consisting of (a) monoalkyl quaternary ammonium salt cationic surfactant having the formula (I):

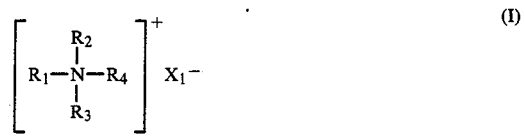

wherein $R_1$ represents an alkyl or alkenyl having 12 to 22 carbon atoms, $R_2$, $R_3$, and $R_4$ independently represent methyl or ethyl, and $X_1$ represents a halogen atom or a methylsulfate residue, (b) ethylene oxide addition quaternary ammonium salt cationic surfactants having the formula (II):

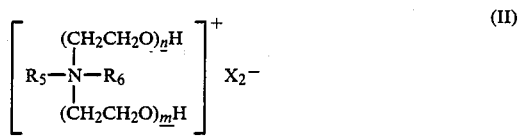

wherein $R_5$ represents an alkyl having 16 to 22 carbon atoms, $R_6$ represents methyl, ethyl, or an alkyl having 16 to 22 carobn atoms, $X_2$ represents a halogen atom or a methylsulfate or ethylsulfate residue, m and n are independently 0 or an integer of at least 1, provided that the sum of m and n is 1 to 30, and (c) imidazoline quaternary ammonium salt cationic surfactants having the formula (III):

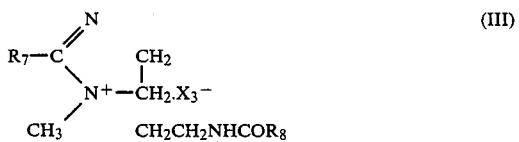

wherein $R_7$ and $R_8$ independently represent an alkyl or alkenyl having 12 to 22 carbon atoms, and $X_3$ represents an halogen atom or a methylsulfate or ethylsulfate residue;

(ii) at least one carboxylate anionic surfactant; and
(iii) at least one amphoteric surfactant and/or (iv) at least one nonionic surfactant, the mole ratio of the components (i)/(ii) being within the range from 4/6 to 8/2.

24 Claims, No Drawings

DETERGENT COMPOSITION CONTAINING A QUATERNARY AMMONIUM CATIONIC SURFACTANT AND A CARBOXYLATE ANIONIC SURFACTANT

CROSS-REFERENCE TO RELATED APPLICATION

This application is a continuation-in-part of Ser. No. 054,342, filed May 26, 1987, now abandoned.

BACKGROUND OF THE INVENTION

1. Field of the Invention

The present invention relates to a detergent composition. More specifically, it relates to a detergent composition suitable for use as, for example, a hair or body shampoo or a garment or dish detergent containing (i) a quaternary ammonium cationic surfactant, (ii) a carboxylate anionic surfactant, and (iii) an amphoteric surfactant and/or (iv) a nonionic surfactant.

2. Description of the Related Art

Conventionally, anionic surfactants and amphoteric surfactants are generally incorporated, as a main foaming detergent, into shampoos. But, when only these surfactants are incorporated into shampoos, although a sufficient detergent power for washing the hair can be obtained, the applicability of the shampoos is not satisfactory, especially when a so-called "squeak" phenomenon in the hair is remarkable. Various attempts have been made to solve this "squeak" problem by formulating, for example, cationic polymers or cationic surfactants, whereby conditioning effects affording, for example, a smoothness to the hair, are desired. The use of cationic polymers, however, causes an accumulation thereof on the hair. On the other hand, the amount of cationic surfactants used in shampoos is limited, since cationic surfactants irritate the skin. Accordingly, shampoos having satisfactory conditioning effects have not been obtained, although products having high conditioning effects are needed.

SUMMARY OF THE INVENTION

Accordingly, the objects of the present invention are to eliminate the above-mentioned disadvantages of the prior art and to provide a detergent composition having an excellent conditioning effect and low skin irritation.

Other objects and advantages of the present invention will be apparent from the following description.

In accordance with the present invention, there is provided a detergent composition comprising, in an aqueous medium, (i) at least one quaternary ammonium cationic surfactant selected from the group consisting of (a) monoalkyl quaternary ammonium salt cationic surfactants having the formula (I):

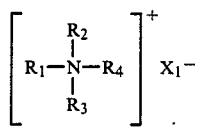

wherein $R_1$ represents an alkyl or alkenyl having 12 to 22 carbon atoms, $R_2$, $R_3$, and $R_4$ independently represent methyl or ethyl, and $X_1$ represents a halogen atom or a methylsulfate residue, (b) ethylene oxide addition quaternary ammonium salt cationic surfactants having the formula (II):

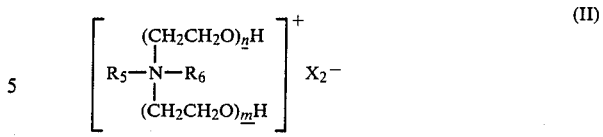

wherein $R_5$ represents an alkyl having 16 to 22 carbon atoms, $R_6$ represents methyl, ethyl, or an alkyl having 16 to 22 carbon atoms, $X_2$ represents a halogen atom or a methylsulfate or ethylsulfate residue, m and n are independently 0 or an integer of at least 1, provided that the sum of n and m is 1 to 30, and (c) imidazoline quaternary ammonium salt cationic surfactants having the formula (III):

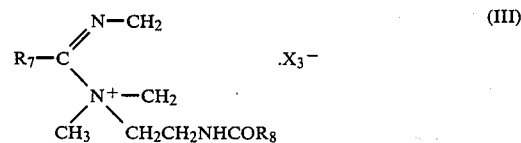

wherein $R_7$ and $R_8$ independently represent an alkyl or alkenyl having 12 to 22 carbon atoms, and $X_3$ represents an halogen atom or a methyl sulfate or ethylsulfate residue;

(ii) at least one carboxylate anionic surfactant, and
(iii) at least one amphoteric surfactant and/or (iv) at least one nonionic surfactant, the mole ratio of the components (i)/(ii) being within the range from 4/6 to 8/2.

DESCRIPTION OF THE PREFERRED EMBODIMENT

The present inventors have made an intensive study of a detergent composition such as a shampoo having a conditioning effect and low skin irritation and, as a result, found that the use of the specified quaternary ammonium cationic surfactants and carboxylate anionic surfactants at a specified ratio and in combination with amphoteric surfactants, and/or nonionic surfactants can provide a detergent composition satisfying the above-mentioned objects.

When anionic surfactants and cationic surfactants are present together in an aqueous solution, complexes are generally formed in the crystalline phase and the complex is precipitated to make the solution turbid, or to cause separation of the complex. Namely, when quaternary ammonium salt type cationic surfactants are mixed in an aqueous solution with anionic surfactants such as sulfonate type surfactants (e.g., higher alkyl sulfonates), sulfuric acid ester salt type surfactants (e.g., salts of higher alcohol sulfates), or phosphoric acid ester salt type surfactants (e.g., salts of polyoxyethylene alkylether phosphonic acid ester), complexes are formed in the crystalline phases at any mole ratio and the resultant complexes are precipitated, and thus the aqueous solution becomes turbid or the complexes are separated from the aqueous solution. But, when monoalkyl quaternary ammonium salt cationic surfactants are combined with carboxylic acid salt anionic surfactants at specific mole ratios in aqueous solutions, the complexes are not formed in the crystalline phases but in the solution, and the resultant complexes are transparent and have excellent conditioning effects and low skin irritation. Nevertheless, although these complexes have the above-mentioned advantages, the foaming power and detergency thereof are not as high as in a conventional shampoo. According to the present invention, the foaming power and the detergency can be advantageously improved, without impairing the desired conditioning effect and the desired skin safety, by incorporating amphoteric surfactants and/or nonionic surfactants into the above-mentioned composition.

The cationic surfactants usable in the present invention are one or more of quaternary ammonium salts having the above-mentioned general formulae (I), (II), and (III). When dialkyl type quaternary ammonium cationic surfactants or other cationic surfactants are used, instead of the quaternary ammonium salts, (I), (II), and (III), crystallines are precipitated and the desired composition cannot be obtained.

Examples of the monoalkyl quaternary ammonium salt cationic surfactants (I) are stearyltrimethylammonium chloride, myristylmethylammonium chloride, and palmityldimethylethylammoniumethyl sulfate.

Examples of the ethylene oxide addition quaternary ammonium salt cationic surfactants (II) are dipolyoxyethylene (2 mol addition) stearylethylammonium bromide and dipolyoxyethylene (4 mol addition) behenylmethylammonium chloride.

In the present invention, any surfactant having one or more —COO— groups may be used as the carboxylate anionic surfactant. Examples of the carboxylate anionic surfactant are as follows:

(A) Fatty acid soap anionic surfactants having the formula:

$$R_9COOM_1$$

wherein $R_9$ represents an alkyl or alkenyl group having 8 to 18 carbon atoms, $M_1$ represents one or more of alkali metals, organic amines, and basic amino acids (e.g., sodium laurate, potassium myristate, sodium oleate, sodium stearate, behenic acid triethanolamine salt); and (B) Ether carboxylate anionic surfactants having the formula:

$$R_{10}(OCH_2CH_2)_xOCH_2COOM_2$$

wherein $R_{10}$ represents an alkyl or alkenyl group having 8 to 22 carbon atoms, x is zero or an integer of 1 to 16, and $M_2$ represents one or more of alkali metals, organic amines, and basic amino acids (e.g., sodium polyoxyethylene (3 mol addition) lauryl ether acetate, sodium polyoxyethylene (6 mol addition) myristyl ether acetate).

As the carboxylate anionic surfactant, a condensation product of a higher fatty acid and an amino acid (e.g., sarcosine, β-alanine, methyl-β-alanine, glutamic acid, glycine, valine, or leucine) may be used. Examples of such carboxylate anionic surfactant are as follows:

(C) N-acylsarcosinate anionic surfactants having the formula:

$$R_{11}CONCH_2COOM_3$$
$$\quad\;\;|\\ \quad\;\;CH_3$$

wherein $R_{11}$ represents an alkyl or alkenyl group having 8 to 18 carbon atoms and $M_3$ represents one or more of alkali metals, organic amines and basic amino acids (e.g., potassium N-lauroylsarcosinate, N-stearoylsarcosinate triethanolamine salt);

(D) N-acrylglutamates represented by $$R_{12}CONHCHCOOM_4$$
$$\quad\;\;\;\;\;\;\;\;\;\;\;\;|\\ \quad\;\;\;\;\;\;\;\;\;\;CH_2CH_2COOM_4$$

wherein $R_{12}$ represents an alkyl or alkenyl group having 8 to 18 carbon atoms and $M_4$ independently represents one or more of alkali metals, organic amines, and basic amino acids;

(E) N-acyl-N-methyl-β-alanine salt anionic surfactant represented by $$R_{13}CONCH_2CH_2COOM_5$$
$$\quad\;\;|\\ \quad\;\;CH_3$$

wherein $R_{13}$ represents an alkyl or alkenyl group having 8 to 18 carbon atoms and $M_5$ represents one or more of alkali metals, organic amines, and basic amino acids; and (F) N-acyl alanine salt anionic surfactant represented by $$R_{14}CONHCH_2CH_2COOM_6$$

wherein $R_{14}$ represents an alkyl or alkenyl group having 8 to 18 carbon atoms and $M_6$ represents one or more of alkali metals, organic amines, and basic amino acids.

Further, as the carboxylate anionic surfactant, there may be used dicarboxylate surfactant (G) having the formula:

$$CH_3(CH_2)_n-CH\underset{\underset{Z}{|}}{\overset{\overset{CH=CH}{\diagup\;\;\;\diagdown}}{\underset{CH=CH}{\diagdown\;\;\;\diagup}}}CH-(CH_2)_s-COOM_7 \quad (G)$$
$$\qquad\qquad\qquad\qquad\qquad\;\; |\\ \qquad\qquad\qquad\qquad\qquad\;\; Z$$

wherein n and s are independently an integer of 3 to 9, period that the sum of n and s is 12, one Z represents a hydrogen atom, the other Z represents —COOM$_8$, and M$_7$ and M$_8$ independently represent one or more alkali metals (e.g., potassium), ammonium, organic amines (e.g., alkanolamine) and a basic amino acids.

The above-mentioned anionic surfactants may be used alone or in any mixture thereof. The present detergent composition must contain the component (i), i.e., the quaternary ammonium salt cationic surfactants, and the component (ii), i.e., carboxylate anionic surfactants, at a mole ratio of the components (i)/(ii) of 4/6 to 8/2, preferably 5/5 to 7/3. When the mole ratio is less than 4/6, the conditioning effect of the resultant detergent composition is reduced. Contrary to this, when the mole ratio is more than 8/2, the skin irritation caused by the resultant detergent composition is unpreferably strong.

Although there are no critical limitations to the total amount of the components (i) and (ii) in the detergent composition, the total amount of the components (i) and (ii) is preferably 0.5% to 20% by weight, more preferably 1% to 15% by weight, based on the total amount of the present detergent composition. When the total amount of the components (i) and (ii) is less than 0.5% by weight, the conditioning effect tends to be decreased because the amount of the surfactants is insufficient. Contrary to this, when the total amount of the components (i) and (ii) is more than 20% by weight, the skin irritation tends to become strong.

The amphoteric surfactants usable in the present invention are those which can be used in conventional shampoos. Typical examples of such amphoteric surfactants are imidazoline amphoteric surfactants such as sodium 2-undecyl-N,N,N-(hydroxyethylcarboxymethyl)-2-imidazoline, 2-cocoyl-2-imidazoliniumhydroxide-1-carboxyethyloxy-2-sodium; betaine amphoteric surfactants such as 2-heptadecyl-N-carboxymethyl-N-hydroxyethyl imidazolinium betaine, betaine lauryl dimethylamino acetate; coconut fatty acid amide dimethylamino acetic acid betaine, laurylsulfo betaine, amine oxides.

These amphoteric surfactants may be used alone or in any mixture thereof. Although there are no critical limitations to the amount of the amphoteric surfactant in the composition, this amount is preferably 0.1% to 20% by weight, especially 5% to 15% by weight, based on the total amount of the composition, in the present detergent composition.

The nonionic surfactants usable in the present invention are those having an HLB of 4 to 20 and alkyl glycosides having the formula (IV):

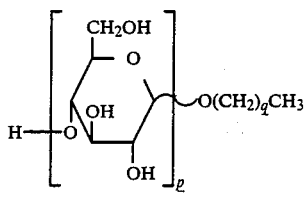

(IV)

wherein p is an integer of 1 to 15 and q is an integer of 7 to 19.

Examples of the nonionic surfactants having an HLB of 4 to 20 are POE (i.e., polyoxyethylene) sorbitane monooleate, POE sorbitane monostearate, POE-sorbitane monooleyl ether, POE-POP alkyl ethers such as POE-POP hydrogenated lanolin, POE-POP glycerine ether, POE lauryl ether; tetraPOE-tetraPOP ethylenediamine condensates such as Tetronic; POE castor oil, POE hardened castor oil, POE castor oil or hardened castor oil derivatives such as POE hardened castor oil monoisostearate, POE hardened castor oil triisostearate, POE hardened castor oil monoglutamate monoisostearate diester, POE hardened castor oil maleate; POE beeswax-lanolin derivatives such as POE sorbitol beeswax; alkanolamides such as coconut fatty acid diethanolamide, lauric monoethanolamide, fatty acid isopropanolamide; POE propylene glycol fatty acid ester, POE alkyl amine, POE fatty acid amide, sucrose fatty acid ester, POE nonylphenyl formaldehyde condensate, alkylethoxydimethylamine oxide, trioleyl phosphoric acid.

Examples of the alkylglycosides (IV) are those having a straight alkyl group with 8 to 20 carbon atoms, in particular, an alkylglucoside having a straight alkyl group with 10 to 16 carbon atoms has an excellent foaming richness, and can be used either individually or as a mixture. The sugar moiety is glucose or an oligosaccharide having glucose as the unit. The number of glucose units may be 1 to 15, preferably 1 to 5, and the bonding between glucoses may be either $\alpha$ or $\beta$, or a mixture thereof.

The amount of the nonionic surfactants having an HLB of 4 to 20 or the alkylglucoside to be used in the present invention is preferably 5 to 70% by weight of the total amount of the composition, more preferably 8 to 60% by weight. With an amount less than 5% by weight, the foam richness is undesirably reduced.

The detergent compositions according to the present invention may contain, in addition to the above-mentioned essential constituents, any conventional ingredients and additives generally used, as optional components, in detergent compositions, as long as the desired properties of the present invention are not adversely affected.

Examples of such optional components are oils such as higher alcohols (e.g., cetyl alcohol, stearyl alcohol), silicone oils (e.g., dimethyl polysiloxanes having a polymerization degree of 4 to 6000, methyl phenyl siloxane), liquid paraffins (e.g., hydrocarbon oils such as squalane, cetyl isooctanoate, distearyl acid ethylene glycol), and ester oils; water-soluble polymers such as methyl cellulose, hydroxyethyl cellulose; cationic polymers such as cationic modified cellulose ether derivatives (e.g., Polymer JR commercially available from Union Carbide Corporation); and polydimethylallyl ammonium chloride (Mercoat 100 commercially available from Merk Co.); copolymers of dimethyldiallylallylammonium chloride and acrylamide (Mercoat 550 commercially available from Merk Co.); the condensate products of polyglycol and polyamine (e.g., polycoat H commercially available from Henkel Corporation); organic acids such as citric acid and lactic acids; hydrogenase such as protease; inorganic salts such as sodium chloride and potassium chloride; anti-bacteria; inorganic builders; fluorescent agents; perfumes or flavors; coloring agents; preservatives; chelating agents; and UV absorbers; and natural extracts of animals and vegetables and the derivatives thereof.

Examples of natural extracts of animals and vegetables and derivatives thereof are licorice, paprika, muirapuama, Japanese barberry, Melaleuca, parasite plant (mistleteo), hollyhock (Malva sylvestris), Cassia tora, Fuccus evanescens C. Ag., scouring rush, oats, Oak moss, spearmint, elm-tree, Robdosia japonika Hara, Ruta graveolens, Inula britannica, sophora Flower, gas-plant, red-berried elder, Lycoperdon perlatum pers., flag (Typha latifolia), pineapple, cabbage, pulsatillae, Zineiber zerumbet Smith, Gloipeltis tenax J. Ag., spicebuth (Pindera sericea), papaia, milesia, Citrus, mulberry tree, Isodon trchocarpas, Sephora flavescens Ait., camphor tree, Iridis semen, banana, Nuphar japonicum DC., Orixa, chickweed, Aralia, Houttuynia cordata, red bean, Cochicum autumnale, eggplant, cherry, Juniper, iris, honeysuckle, sorrel, Tilia europea, bead tree, celery, geranium, Stephania cephalantha Hayata, strawberry, creeping pine, turmerie, Lamium album var. barbatum Fr. it Sav., tea plant, orange, sage, ivy, Sambucus nigra, Juniperus communis, Achilea millefolium, Rentha piperita, viscum alkum, mallow, Liquisticum officinale Kitagawa, Thymus valgaris, Swertia japonika, thyme, clove-tree, citrus unshiu peel, algae, chlorella, Japanese angelica root, bitter orange peel, tomato, Hypericacear hypericum, Clematis apiifolia DC. var. biternata Makino, carrot, garlic, wild rose, Betura lenta, parsley, gentia, peppermint, Ononis, Hamamelis, rose, fennel, horsetail, saffron, watercress, Saponaria officinalis, hawthorn, crane's bill, loquat, Gynura japonica, grape, grape leaf, ivy, snake gourd, nettle, linden-tree, hop, Japanese pepper, Cortinellus shiitake, pine-cone, chestnut tree, Menyanthes trifoliata, Sapindus mukurossi Gaerton, melissa, melilot, peach, Rodger's bronze leaf, eucalyptus, Rehmannia glutinosa Libosh., gromwell root, creeping saxifrage, oil-soluble Arnica, oil-soluble calendula, oil-soluble, oil-soluble wild rose, Phaeophyta, Valeriana fauriei Briq., oil-soluble coix seed, lily, garlic iodide, mugwort, beefsteak plant, Tilia japonica Simk, Spiraeu japonica, apple, oats, herbaceous peony, apricot, letus, Rosemary, lemon, Anthemis nobilis, Rose fruit, burnet, white birch, raspberry, stebia, water-soluble Arnica, Scutellaria root, Hedera, Cinchona, cucumber, Aloe, burdock, Cape jasmine, grapefruit, phellodendron bark, Coptis japonica Makino, Styracaceae benzoin Dryand., red grape, Gambir, Althaea officinalois, sweet hydrangea leaf, Ginger, capsicum tincture, rosin colophony, natural rubber latex, gum arabic, Ichthammol, cantaris tincture, China root, Polyporaceae, polyporus, Japanese persimmon, collagen, Bacillus biphydus, pectin, yeast, royal jelly, water-soluble plancenta extract, bees honey, shellac.

EXAMPLES

The present invention will now be further illustrated by, but is by no means limited to, the following Examples. The effects were evaluated by the following test and evaluation methods.

TEST AND EVALUATION METHODS

1. Conditioning effect

The conditioning effects were evaluated by a panel consisting of 15 women for "smoothness", "glossiness", and "combability" as follows.

A 12 g amount of a sample composition was actually applied to the hair, and after rinsing with lukewarm water, the hair was air dried. The hair was organoleptically evaluated for each item. The evaluation was carried out by the following four grades.

2. Skin irritation

It is known in the art that skin irritation can be evaluated by a degree of the denaturing activity for proteins (i.e., "protein denaturation") of surfactants or the compositions thereof (see JP-B-59-42038). The skin irritation was evaluated by a protein denaturation in this manner in the following Examples.

The protein denaturation was determined as follows.

A sample composition was added to an egg white albumin solution buffered to a pH of 7 so that the sample concentration was 1%. The denaturing percentage of the egg white albumin was determined by using an absorption peak at 220 nm as follows.

$$\text{Protein denaturation (\%)} = \frac{H_0 - H_S}{H_0} \times 100$$

wherein $H_0$: height of absorption peak of egg white albumin at 220 nm $H_S$: height of absorption peak at 220 nm when the sample was added to the egg white albumin buffered solution.

The evaluation was carried out by the following four-stage standards.

⊚ : Very slight skin irritation (i.e., denaturation is less than 30%)

o: Little skin irritation (i.e., denaturation is not less than 30% but less than 60%)

Δ: Middling skin irritation (i.e., denaturation is not less than 60% but less than 80%)

x: Strong skin irritation (i.e., denaturation is 80% or more)

EXAMPLES 1 TO 7 COMPARATIVE EXAMPLES 1 TO 7

The detergent compositions having the formulations listed in Table 1 and the rinsing effects and skin irritation thereof were evaluated as mentioned above. The results of Examples 1 to 7 and Comparative Examples 1 to 7 are shown in Table 1.

TABLE 1 (unit: % by weight)

| Ingredient | Ave. M.W. | Example 1 | Example 2 | Comparative Example 1 | Comparative Example 2 | Comparative Example 3 | Comparative Example 4 | Example 3 | Example 4 | Example 5 | Example 6 | Example 7 | Comparative Example 5 | Comparative Example 6 | Comparative Example 7 |
|---|---|---|---|---|---|---|---|---|---|---|---|---|---|---|---|
| C$_{12}$ alkyltrimethyl ammonium chloride | 264 | 1.85 | — | 1.85 | 1.85 | — | — | — | — | — | — | — | — | — | — |
| C$_{18}$ alkyltrimethyl ammonium chloride | 348 | — | 3.65 | — | — | 1.39 | 2.09 | 2.78 | 3.48 | 4.18 | 4.87 | 5.57 | 6.26 | 0.18 | 18.6 |
| Imidazolium betaine | — | 10 | — | 10 | 10 | — | — | — | — | — | — | — | — | 10 | 10 |
| Betaine lauryldimethylamino acetate | — | — | 15 | — | — | 8 | 8 | 8 | 8 | 8 | 8 | 8 | 8 | — | — |
| Sodium laurate | 222 | 0.67 | — | — | — | — | — | — | — | — | — | — | — | 0.062 | 6.39 |
| Potassium myristoyl glutamate | 433 | — | 1.95 | — | — | 6.93 | 6.06 | 5.20 | 4.33 | 3.46 | 2.60 | 1.73 | 0.87 | — | — |
| Sodium lauryl sulfate | 288 | — | — | 0.86 | — | — | — | — | — | — | — | — | — | — | — |
| Sodium C$_{14}$ α-olefin sulfonate | 340 | — | — | — | 1.02 | — | — | — | — | — | — | — | — | — | — |
| Water | — | ← Balance → | | | | | | | | | | | | | |
| Molar ratio (Cationic surfactant/Anionic surfactant) | | 7/3 | 7/3 | 7/3 | 7/3 | 2/8 | 3/7 | 4/6 | 5/5 | 6/4 | 7/3 | 8/2 | 9/1 | 6.5/3.5 | 6.5/3.5 |
| Conditioning effect | | | | | | | | | | | | | | | |
| Smoothness | | ⊚ | ⊚ | x | x | Δ | O | ⊚ | ⊚ | ⊚ | ⊚ | ⊚ | o | x | ⊚ |
| Glossiness | | ⊚ | ⊚ | x | x | x | Δ | O | ⊚ | ⊚ | ⊚ | ⊚ | o | x | ⊚ |
| Combability | | ⊚ | ⊚ | x | x | x | Δ | ⊚ | ⊚ | ⊚ | ⊚ | o | Δ | x | ⊚ |
| Skin irritation (protein denaturation) | | ⊚ | ⊚ | x | x | o | O | ⊚ | ⊚ | ⊚ | ⊚ | o | x | o | x |

⊚ : Very good
o: Good
Δ: Fair
x: Poor

EXAMPLE 8

The hair shampoo having the following formulation (i.e., cationic surfactant/anionic surfactant=6/4 at molar ratio) was prepared and the resultant shampoo was evaluated in the same manner as in Examples 1 to 7.

| Ingredient | % by weight |
|---|---|
| Sodium 2-undecyl-N,N,N-(hydroxyethyl-carboxymethyl)-2-imidazoline | 15.0 |
| Polymer-JR-400 (Union Carbide Corp.) | 0.2 |
| $C_{16}$ alkyltrimethyl ammonium chloride (Ave. molecular weight = 320) | 1.92 |
| Sodium lauroylmethyl-$\beta$-alanine (Ave. molecular weight = 307) | 1.23 |
| Propylene glycol | 5.0 |
| Polyoxyethylene (Ave. 40 mole) hydrogenated castor oil derivative | 2.0 |
| Coloring agent | q.s. |
| Perfume | q.s. |
| Deionized water | Balance |

This hair shampoo had excellent conditioning effects and only slight irritation of the skin.

EXAMPLE 9

The body shampoo having the following formulation (i.e., cationic surfactant/anionic surfactant=7/3 at mole ratio) was prepared and was evaluated in the same manner as in Examples 1 to 8.

| Ingredient | % by weight |
|---|---|
| Betaine lauryl dimethylamino acetate | 10.0 |
| $C_{22}$ alkenylmethyl ammonium chloride (Ave. molecular weight = 401) | 2.81 |
| Sodium lauroyl sarcosinate (Ave. molecular weight = 293) | 0.88 |
| Dipropylene glycol | 8.0 |
| Aloe extract | 0.5 |
| Coloring agent | q.s. |
| Perfume | q.s. |
| Preservative | q.s. |
| Chelating agent | q.s. |
| Deionized water | Balance |

This body shampoo had excellent conditioning effects and only slight irritation of the skin.

EXAMPLE 10

The hair shampoo having the following formulation (i.e., cationic surfactant/anionic surfactant=7/3 at mole ratio) was prepared and the resultant shampoo was evaluated in the same manner as in Examples 1 to 9.

| Ingredient | % by weight |
|---|---|
| Sodium 2-undecyl-N,N,N-(hydroxyethyl-carboxymethyl)-2-imidazoline | 20.0 |
| Polycoat H (Henkel Corp.) | 2.0 |
| Coconut oil fatty acid diethanolamide | 5.0 |
| $C_{16}$ alkyltrimethyl ammonium chloride (Ave. molecular weight = 320) | 2.24 |
| Sodium lauroyl alanine (Ave. molecular weight = 293) | 0.88 |
| Propylene glycol | 3.0 |
| Coloring agent | q.s. |
| perfume | q.s. |
| Deionized water | Balance |

The hair shampoo had excellent conditioning effects and only slight irritation of the skin.

EXAMPLE 11

The hair shampoo having the following formulation (i.e., cationic surfactant/anionic surfactant=6/4 at mole ratio) was prepared and the resultant shampoo was evaluated in the same manner as in Examples 1 to 10.

| Ingredient | % by weight |
|---|---|
| Betaine lauryldimethylamino acetate | 20.0 |
| Polycoat-H | 1.0 |
| Coconut fatty acid monoethanolamide | 0.5 |
| $C_{18}$ alkyltrimethyl ammonium chloride (Ave. molecular weight = 348) | 2.09 |
| Sodium lauroylsarcosinate (Ave. molecular weight = 293 | 1.17 |
| Coloring agent | q.s. |
| Perfume | q.s. |
| Deionized water | Balance |

This hair shampoo had excellent conditioning effect and only slight irritation of the skin.

EXAMPLES 12 TO 18 AND COMPARATIVE EXAMPLES 8 TO 14

TEST AND EVALUATION METHODS (1) Rinsing effect (Softness test)

Ten sheets of cotton cloth 30 cm×80 cm were washed by hand in 5 liters of a 0.3% aqueous detergent solution at a water temperature of 30° C., and after drying in air, organoleptic tests were conducted by a panel of 10.

The evaluation was made according to the following criteria.

⊚ ... 8 to 10 panel members felt that the finish was softer, compared with a standard detergent;

o ... 6 to 8 panel members felt that the finish was softer, compared with a standard detergent;

Δ ... 3 to 5 panel members felt that the finish was softer, compared with a standard detergent;

x ... 2 panel members or less felt that the finish was softer, compared with a standard detergent.

Detergent compositions having the formulations shown in Table 2 were prepared and the rinsing (softness) and skin irritation effects thereof were evaluated.

TABLE 2

(Unit: wt. %)

| Component | Average molecular weight | Example 12 | Example 13 | Comparative Example 8 | Comparative Example 9 | Comparative Example 10 | Comparative Example 11 | Example 14 | Example 15 | Example 16 | Example 17 | Example 18 | Comparative Example 12 | Comparative Example 13 | Comparative Example 14 |
|---|---|---|---|---|---|---|---|---|---|---|---|---|---|---|---|
| C₁₂ alkyltrimethylammonium chloride | 264 | 1.85 | — | 1.85 | 1.85 | — | — | — | — | — | — | — | — | — | — |
| C₁₈ alkyltrimethylammonium chloride | 348 | — | 3.65 | — | — | 1.39 | 2.09 | 2.78 | 3.48 | 4.18 | 4.48 | 5.57 | 6.26 | 0.35 | 18.6 |
| Polyoxyethylene nonylphenylether (EO = 10) | | 10 | — | 10 | 10 | 8 | 8 | 8 | 8 | 8 | 8 | 8 | 8 | 10 | 10 |
| Polyoxyethylene dodecyl ether (EO = 15) | | — | 15 | — | — | — | — | — | — | — | — | — | — | — | — |
| Sodium laurate | 222 | 0.67 | — | — | — | — | — | — | — | — | — | — | — | — | — |
| Potassium myristoyl glutamate | 433 | — | 1.95 | — | — | 6.93 | 6.06 | 5.20 | 4.33 | 3.46 | 2.06 | 1.73 | 0.87 | 0.12 | 6.39 |
| Sodium lauryl sulfate | 288 | — | — | 0.86 | — | — | — | — | — | — | — | — | — | — | — |
| C₁₄-α-sodium olefin sulfonate | 340 | — | — | — | 1.02 | — | — | — | — | — | — | — | — | — | — |
| Water | | Balance | " | " | " | " | " | " | " | " | " | " | " | " | " |
| Molar ratio Cationic surfactant / Anionic surfactant | | 7/3 | 7/3 | 7/3 | 7/3 | 2/8 | 3/7 | 4/6 | 5/5 | 6/4 | 7/3 | 8/2 | 9/1 | 6.5/3.5 | 6.5/3.5 |
| Rinsing effect | | ⊚ | ⊚ | × | × | △ | ○ | ⊚ | ⊚ | ⊚ | ⊚ | ⊚ | ○ | × | ⊚ |
| Skin irritation (protein denaturation) | | ⊚ | ⊚ | × | × | ○ | ○ | ⊚ | ⊚ | ⊚ | ⊚ | ○ | × | ○ | × |

EXAMPLE 19

A detergent composition for washing cloth and having the following formulation was prepared (molar ratio of cationic surfactant/anionic surfactant=7/3), and evaluated by the same method as used in Examples 12 to 18.

| Components | % by weight |
| --- | --- |
| Polyoxyethylene dodecyl ether (EO = 15) | 15.0 |
| Polyoxyethylene dodecyl ether (EO = 3) | 3.0 |
| $C_{16}$ alkyltrimethylammonium chloride (average MW 320) | 2.24 |
| Sodium lauroyl methyl-$\beta$-alanine (average MW 307) | 0.92 |
| N-lauryldimethylaminoacetic acid betaine | 4.0 |
| Colorant, perfume | q.s. |
| Deionized water | balance |
| Sodium lauroylsarcosinate (average MW = 293) | 1.17 |
| Colorant, perfume | q.s. |
| Deionized water | balance |

This detergent composition for washing cloth was found to have an excellent rinsing effect (softness) and little skin irritation.

EXAMPLES 21 TO 27 AND COMPARATIVE EXAMPLES 15 TO 21

Detergent compositions having the formulations shown in Table 3 were prepared, and the rinsing (softness) and skin irritation effects thereof are shown, together with Comparative Examples, in Table 3. Examples having additives, etc., formulated therein are also shown.

TABLE 3

(Unit: wt. %)

| Component | Average molecular weight | Example 21 | Example 22 | Comparative Example 15 | Comparative Example 16 | Comparative Example 17 | Comparative Example 18 | Example 23 | Example 24 | Example 25 | Example 26 | Example 27 | Comparative Example 19 | Comparative Example 20 | Comparative Example 21 |
| --- | --- | --- | --- | --- | --- | --- | --- | --- | --- | --- | --- | --- | --- | --- | --- |
| 1 *R = 20 m + n = 10 | 787 | 5.51 | — | 5.51 | 5.51 | — | — | — | — | — | — | — | — | — | — |
| 1 *R = 18 m + n = 4 | 495 | — | 3.47 | — | — | 1.98 | 2.97 | 3.96 | 4.95 | 5.94 | 6.93 | 7.92 | 8.91 | 0.17 | 19.30 |
| Imidazolium betaine | | 10 | — | 10 | 10 | — | — | — | — | — | — | — | — | 10 | 10 |
| Lauryldimethylaminoaceticacid betaine | | — | 15 | — | — | 8 | 8 | 8 | 8 | 8 | 8 | 8 | 8 | — | — |
| Sodium laurate | 222 | 0.67 | — | — | — | — | — | — | — | — | — | — | — | 0.04 | 4.66 |
| Potassium myristoyl glutamate | 433 | — | 1.30 | — | — | 6.93 | 6.06 | 5.20 | 4.33 | 3.46 | 2.60 | 1.73 | 0.87 | — | — |
| Sodium lauryl sulfate | 288 | — | — | 0.86 | — | — | — | — | — | — | — | — | — | — | — |
| $C_{14}$-$\alpha$-sodium olefin sulfonate | 340 | — | — | — | 1.02 | — | — | — | — | — | — | — | — | — | — |
| Water | | Balance | ″ | ″ | ″ | ″ | ″ | ″ | ″ | ″ | ″ | ″ | ″ | ″ | ″ |
| Molar ratio $\frac{\text{Cationic surfactant}}{\text{Anionic surfactant}}$ | | 7/3 | 7/3 | 7/3 | 7/3 | 2/8 | 3/7 | 4/6 | 5/5 | 6/4 | 7/3 | 8/2 | 9/1 | 6.5/3.5 | 6.5/3.5 |
| Rinsing effect | | | | | | | | | | | | | | | |
| Softness | | ⊚ | ⊚ | x | x | Δ | o | ⊚ | ⊚ | ⊚ | ⊚ | ⊚ | o | x | ⊚ |
| Luster | | ⊚ | ⊚ | x | x | x | Δ | o | ⊚ | ⊚ | ⊚ | ⊚ | o | x | ⊚ |
| Comb-out property | | ⊚ | ⊚ | x | x | x | Δ | ⊚ | ⊚ | ⊚ | ⊚ | o | Δ | x | ⊚ |
| Skin irritation (protein denaturation) | | ⊚ | ⊚ | x | x | o | o | ⊚ | ⊚ | ⊚ | ⊚ | o | x | o | x |

$$1* \begin{bmatrix} (CH_2CH_2O)\ nH \\ | \\ R-N-CH_3 \\ | \\ (CH_2CH_2O)\ mH \end{bmatrix}^+ CL^-$$

This detergent composition for washing cloth was found to have an excellent rinsing effect (softness) and little skin irritation.

EXAMPLE 20

A detergent composition for washing cloth and having the following composition was prepared (molar ratio of cationic surfactant/anionic surfactant=6/4), and evaluated by the same method as used in Examples 12 to 19.

| Components | % by weight |
| --- | --- |
| Polyoxyethylene octylphenyl ether (EO = 10) | 12.0 |
| Polyoxyethylene octylphenyl ether (EO = 2) | 2.0 |
| $C_{16}$ alkyltrimethylammonium chloride (average MW = 320) | 1.92 |

EXAMPLE 28

A hair shampoo composition having the following formulation was prepared (molar ratio of cationic surfactant/anionic surfactant=6/4), and evaluated by the same method as used in Examples 21 to 27.

| Components | % by weight |
| --- | --- |
| Sodium 2-undefyl-N,N,N(hydroxyethyl-carboxylmethyl)-2-imidazoline | 15.0 |
| Polymer-JR-400 (produced by Union Carbide Co.) | 0.2 |
| Cationic surfactant (R: 18, m + n = 2)*[1] (average MW = 407) | 2.44 |
| Sodium lauroyl methyl-$\beta$-alanine (average MW = 307) | 1.23 |
| Propylene glycol | 5.0 |
| Polyoxyethylene (average 40 mol) hardened castor oil derivative | 2.0 |
| Colorant, perfume | q.s. |

| Components | % by weight |
|---|---|
| Deionized water | balance |

*1:
$$\left[\begin{array}{c}(CH_2CH_2O)\,nH \\ | \\ R-N-CH_3 \\ | \\ (CH_2CH_2O)\,mH\end{array}\right]^+ \quad CL^-$$

This hair shampoo was found to have an excellent rinsing effect and little skin irritation.

EXAMPLE 29

A body shampoo having the following formulation was prepared (molar ratio of cationic surfactant/anionic surfactant=7/3) and evaluated by the same method as used in Examples 21 to 28.

| Components | % by weight |
|---|---|
| Lauryldimethylaminoacetic acid betain | 10.0 |
| Cationic surfactant (R: 18, m + n = 2)*1 (average MW = 407) | 2.85 |
| Sodium lauroylsarcosinate (average MW = 293) | 0.88 |
| Dipropylene glycol | 8.0 |
| Aloe extract | 0.5 |
| Colorant, perfume | q.s. |
| Preservative, chelating agent | q.s. |
| Deionized water | balance |

*1: see Example 28

This body shampoo was found to have an excellent rinsing effect and little skin irritation.

EXAMPLE 30

A body shampoo having the following formulation was prepared (molar ratio of cationic surfactant/anionic surfactant=7/3) and evaluated by the same method as used in Examples 21 to 29.

| Components | % by weight |
|---|---|
| Sodium 2-undecyl-N,N,N-(hydroxyethyl-carboxymethyl)2-imidazoline | 20.0 |
| Polycoat H | 2.0 |
| Coconut fatty acid diethanolamide | 5.0 |
| Cationic surfactant (R: 18, m + 2 = 4)*1 (average MW = 495) | 3.47 |
| Sodium lauroylsarcosinate (average MW = 293) | 0.88 |
| Colorant, perfume | q.s. |
| Deionized water | balance |

*1: see Example 28

This hair shampoo was found to have an excellent rinsing effect and little skin irritation.

EXAMPLE 31

A body shampoo having the following formulation was prepared (molar ratio of cationic surfactant/anionic surfactant=6/4) and evaluated according to the same method as in Examples 21 to 30.

| Components | % by weight |
|---|---|
| Sodium 2-undecyl-N,N,N-(hydroxyethyl-carboxymethyl)-2-imidazoline | 20.0 |
| Polycoat H | 1.0 |
| Cationic surfactant (R: 20, M + n = 10)*1 (average MW = 787) | 4.72 |
| Sodium lauroylsarcosinate (average MW = 293) | 1.17 |
| Dipropylene glycol | 1.0 |
| Colorant, perfume | q.s. |
| Deionized water | balance |

*1: see Example 28

This hair shampoo was found to have an excellent rinsing effect and little skin irritation.

EXAMPLES 32 TO 38, COMPARATIVE EXAMPLES 22 TO 28

Detergent compositions having the formulations shown in Table 4 were prepared, and the rinsing and skin irritation effects are shown, together with Comparative Examples, in Table 4. Examples having additives, etc. formulated therein are also shown.

The imidazoline type quaternary ammonium salt type cationic surfactant used in Examples 32 to 38 and Comparative Examples 22 to 28 had the formula shown below:

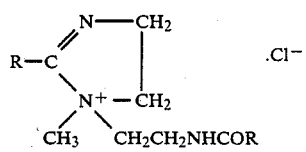

TABLE 4

(Unit: wt. %)

| Component | Average molecular weight | Example 32 | Example 33 | Comparative Example 22 | Comparative Example 23 | Comparative Example 24 | Comparative Example 25 | Example 34 | Example 35 | Example 36 | Example 37 | Example 38 | Comparative Example 26 | Comparative Example 27 | Comparative Example 28 |
|---|---|---|---|---|---|---|---|---|---|---|---|---|---|---|---|
| Imidazoline type quaternary ammonium salt type cationic surfactant (R = 12) | 527 | 3.69 | — | 3.69 | 3.69 | — | — | — | — | — | — | — | — | — | — |
| Imidazoline type quaternary ammonium salt type cationic surfactant (R = 18) | 695 | — | 7.30 | — | — | 2.09 | 3.13 | 4.17 | 5.21 | 6.26 | 7.30 | 8.34 | 9.38 | 0.17 | 22.62 |
| Imidazolium betaine | 222 | 10 | — | 10 | 10 | — | — | — | — | — | — | — | — | — | — |
| Lauryldimethylaminoacetic acid betaine | 433 | — | 15 | — | 8 | 8 | 8 | 8 | 8 | 8 | 8 | 8 | 8 | 10 | 10 |
| Sodium laurate | 288 | 0.67 | — | — | — | — | — | — | — | — | — | — | — | — | — |
| Potassium myristoyl glutamate | 340 | — | 1.95 | — | — | 5.20 | 4.55 | 3.90 | 3.25 | 2.60 | 1.95 | 1.30 | 0.65 | 0.03 | 3.89 |
| Sodium lauryl sulfate | | — | — | 0.86 | — | — | — | — | — | — | — | — | — | — | — |
| $C_{14}$-α-sodium olefin sulfonate | | — | — | — | 1.02 | — | — | — | — | — | — | — | — | — | — |
| Water | | Balance | " | " | " | " | " | " | " | " | " | " | " | " | " |
| Cationic surfactant / Anionic surfactant (molar ratio) | | 7/3 | 7/3 | 7/3 | 7/3 | 2/8 | 3/7 | 4/6 | 5/5 | 6/4 | 7/3 | 8/2 | 9/1 | 6.5/3.5 | 6.5/3.5 |
| Rinsing effect | | | | | | | | | | | | | | | |
| Smoothness | | ⊚ | ⊚ | × | × | △ | ○ | ⊚ | ⊚ | ⊚ | ⊚ | ⊚ | ○ | × | ⊚ |
| Luster | | ⊚ | ⊚ | × | × | × | △ | ○ | ⊚ | ⊚ | ⊚ | ⊚ | ○ | × | ⊚ |
| Comb-out property | | ⊚ | ⊚ | × | × | × | △ | ⊚ | ⊚ | ⊚ | ⊚ | ○ | △ | × | ⊚ |
| Skin irritation (protein denaturation) | | ⊚ | ⊚ | × | × | ○ | ○ | ⊚ | ⊚ | ⊚ | ⊚ | ○ | × | ○ | × |

EXAMPLE 39

A hair shampoo having the following formulation was prepared (molar ratio of cationic surfactant/anionic surfactant=6/4) and evaluated by the same method as used in Examples 32 to 38.

| Components | % by weight |
| --- | --- |
| Sodium 2-undecyl-N,N,N-(hydroxyethyl-carboxymethyl)2-imidazoline | 15.0 |
| Polymer JR-400 (produced by Union Carbide Co.) | 0.2 |
| Imidazoline type quaternary ammonium salt type cationic surfactant [R = 16 (average MW = 639)] | 3.83 |
| Sodium lauroylmethyl-β-alanine (average MW = 307) | 1.23 |
| Propylene glycol | 5.0 |
| Polyoxyethylene (average 40 mol) hardened castor oil derivative | 2.0 |
| Colorant, perfume | q.s. |
| Deionized water | balance |

This hair shampoo was found to have an excellent rinsing effect and little skin irritation.

EXAMPLE 40

A body shampoo having the following formulation was prepared (molar ratio of cationic surfactant/anionic surfactant=7/3) and evaluated by the same method as in Examples 32 to 39.

| Components | % by weight |
| --- | --- |
| Betaine lauryldimethylaminoacetate | 10.0 |
| Imidazoline type quaternary ammonium salt type cationic surfactant [R = 20 (average MW = 751)] | 5.26 |
| Sodium lauroylsarcosinate (average MW = 293) | 0.88 |
| Dipropylene glycol | 8.0 |
| Aloe extract | 0.5 |
| Colorant, perfume | q.s. |
| Preservative, chelating agent | q.s. |
| Deionized water | balance |

This body shampoo was found to have an excellent rinsing effect and little skin irritation.

EXAMPLE 41

A body shampoo having the following formulation was prepared (molar ratio of cationic surfactant/anionic surfactant=7/3) and evaluated by the same method as used in Examples 32 to 40.

| Components | % by weight |
| --- | --- |
| Sodium 2-undecyl-N,N,N—(hydroxyethyl-carboxymethyl)-2-imidazoline | 20.0 |
| Polycoat H | 2.0 |
| Imidazoline type quaternary ammonium salt type cationic surfactant*[1] (average MW = 715) | 5.01 |
| Sodium lauroyl methyl-β-alanine (average MW = 307) | 0.92 |
| Propylene glycol | 3.0 |
| Colorant, perfume | q.s. |
| Deionized water | balance |

[1]* 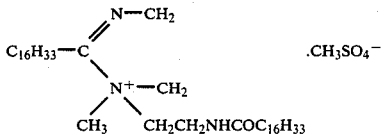

The hair shampoo was found to have an excellent rinsing effect and little skin irritation.

EXAMPLES 42 TO 48, COMPARATIVE EXAMPLES 29 TO 35

Detergent compositions having the formulations shown in Table 5 were prepared, and the rinsing and skin irritation effects thereof are shown, together with Comparative Examples, in Table 5. Examples having additives, etc. formulated therein are also shown.

TABLE 5

(Unit: wt. %)

| Component | Average molecular weight | Example | | Comparative Example | | | | Example | | | | | Comparative Example | | |
|---|---|---|---|---|---|---|---|---|---|---|---|---|---|---|---|
| | | 42 | 43 | 29 | 30 | 31 | 32 | 44 | 45 | 46 | 47 | 48 | 33 | 34 | 35 |
| Compound of the formula (III) (R$_7$ = 12, X$_3$ = Cl) | 527 | 3.69 | — | 3.69 | 3.69 | — | — | — | — | — | — | — | — | — | — |
| Compound of the formula (II) (R$_5$ = 18, R$_6$ = 1, m + n = 4, X$_2$ = Cl) | 495 | — | 3.47 | — | — | 1.98 | 2.97 | 3.96 | 4.95 | 5.94 | 6.93 | 7.92 | 8.91 | 0.17 | 19.30 |
| POE nonylphenyl ether (EO = 10) | | 10 | 10 | 10 | 10 | 10 | 10 | 10 | 10 | 10 | 10 | 10 | 10 | 10 | 10 |
| POE dodecyl (EO = 15) | | — | 15 | — | — | — | — | — | — | — | — | — | — | — | — |
| Sodium laurate | 222 | 0.67 | — | — | — | — | — | — | — | — | — | — | — | — | — |
| Potassium myristoyl glutamate | 433 | — | 1.30 | — | — | 6.93 | 6.06 | 5.20 | 4.33 | 3.46 | 2.60 | 1.73 | 0.87 | 0.04 | 4.66 |
| Sodium lauryl sulfate | 288 | — | — | 0.86 | — | — | — | — | — | — | — | — | — | — | — |
| C$_{14}$-α-sodium olefin sulfonate | 340 | — | — | — | 1.02 | — | — | — | — | — | — | — | — | — | — |
| Water | | Balance | " | " | " | " | " | " | " | " | " | " | " | " | " |
| Cationic surfactant / Anionic surfactant (molar ratio) | | 7/3 | 7/3 | 7/3 | 7/3 | 2/8 | 3/7 | 4/6 | 5/5 | 6/4 | 7/3 | 8/2 | 9/1 | 6.5/3.5 | 6.5/3.5 |
| Rinsing effect | | | | | | | | | | | | | | | |
| Smoothness | | ◎ | ◎ | x | x | △ | ○ | ◎ | ◎ | ◎ | ◎ | ◎ | ○ | x | ◎ |
| Luster | | ○ | ◎ | x | x | x | △ | ○ | ◎ | ◎ | ◎ | ◎ | ○ | x | ◎ |
| Comb-out property | | ○ | ○ | x | x | x | △ | ◎ | ◎ | ◎ | ◎ | ◎ | △ | x | ◎ |
| Skin irritation (protein denaturation) | | ◎ | ◎ | x | x | ○ | ○ | ◎ | ◎ | ◎ | ◎ | ○ | x | ○ | x |

EXAMPLE 49

A shampoo having the following formulation was prepared (molar ratio of cationic surfactant/anionic surfactant=6/4), and evaluated by the same method as used in Examples 42 to 48.

| Components | % by weight |
| --- | --- |
| Polyoxyethylene dodecyl ether (EO = 12) | 15.0 |
| Polymer JR-400 (produced by Union Carbide Co.) | 0.2 |
| Compound of the formula (II) [$R_5$ = 18, $R_6$ = 1, m + n = 2, average MW = 407, $X_2$ = Cl] | 2.44 |
| Sodium lauroylmethyl-$\beta$-alanine (average MW = 307) | 1.23 |
| Propylene glycol | 5.0 |
| Polyoxyethylene (average 40 mol) hardened castor oil derivative | 2.0 |
| Colorant, perfume | q.s. |
| Deionized water | balance |

The shampoo was found to have an excellent rinsing effect and little skin irritation.

EXAMPLE 50

A body shampoo having the following formulation was prepared (molar ratio of cationic surfactant/anionic surfactant=7/3) and evaluated by the same method as used in Examples 42 to 49.

| Components | % by weight |
| --- | --- |
| Polyoxyethylene octylphenyl ether (EO = 10) | 10.0 |
| Compound of the formula (II) [$R_5$ = 18, $R_6$ = 1, m + 2, = 2, average MW = 407, $X_2$ = Cl] | 2.85 |
| Sodium lauroylsarcosinate (average MW = 293) | 0.88 |
| Dipropylene glycol | 8.0 |
| Aloe extract | 0.5 |
| Colorant, perfume | q.s. |
| Preservative, chelating agent | q.s. |
| Deionized water | balance |

This body shampoo was found to have an excellent rinsing effect and little skin irritation.

EXAMPLE 51

A body shampoo having the following formulation was prepared (molar ratio of cationic surfactant/anionic surfactant=7/3) and evaluated by the same method as used in Examples 42 to 50.

| Components | % by weight |
| --- | --- |
| Polyoxyethylene oleyl ether (EO = 8) | 20.0 |
| Polycoat H | 2.0 |
| Coconut fatty acid diethanolamide | 5.0 |
| Compound of the formula (II) [$R_5$ = 18, $R_6$ = 1, M = n = 4, average MW = 495, $X_2$ = Cl] | 3.47 |
| Sodium lauroylsarcosinate (average MW = 293) | 0.88 |
| Propylene glycol | 3.0 |
| Colorant, flavor | q.s. |
| Deionized water | balance |

This hair shampoo was found to have an excellent rinsing effect and little skin irritation.

EXAMPLE 52

A body shampoo having the following formulation was prepared (molar ratio of cationic surfactant/anionic surfactant=6/4) and evaluated by the same method as used in Examples 42 to 51.

| Components | % by weight |
| --- | --- |
| Sodium 2-undecyl-N,N,N-(hydroxyethyl-carboxymethyl)-2-imidazoline | 2.0 |
| Polycoat H | 1.0 |
| Coconut fatty acid diethanolamide | 0.5 |
| Compound of the formula (II) [$R_5$ = 20, $R_6$ = 1, m + n = 10, average MW = 787, $X_2$ = Cl] | 4.72 |
| Sodium lauroylsarcosinate (average MW = 293) | 1.17 |
| Polyoxyethylene dodecyl ether (EO = 14) | 10.0 |
| Dipropylene glycol | 1.0 |
| Colorant, perfume | q.s. |
| Deionized water | balance |

This body shampoo was found to have an excellent rinsing effect and little skin irritation.

EXAMPLE 53

A liquid detergent for clothing having the following formulation was prepared (molar ratio of cationic surfactant/anionic surfactant=5/5) and the softness of the clothing after washing was organoleptically evaluated.

| Components | % by weight |
| --- | --- |
| Polyoxyethylene dodecyl ether (EO = 14) | 30.0 |
| Compound of the formula (II) [$R_5$ = 18, $R_6$ = 1, m + n = 4, average MW = 495, $X_2$ = Cl] | 4.95 |
| Sodium lauroyl methyl-$\beta$-alanine (average MW = 307) | 3.07 |
| Lauroyldimethylaminoacetic acid betaine | 5.0 |
| Fluorescent dye | 0.2 |
| Ethanol | 8.0 |
| Colorant, perfume | q.s. |
| Sodium hydroxide | q.s. |
| Deionized water | balance |

This liquid detergent for clothing was found to have excellent softening and washing effects.

EXAMPLES 54 TO 61 AND COMPARATIVE EXAMPLES 36 TO 42

Method of evaluating foam richness

An aqueous 10% solution of a sample was foamed in hair and the richness of foam was evaluated by 10 members of a panel according to the following standars:

⊚ ... Rich foam
Δ ... Average foam
x ... Foam showed no richness

Detergent compositions having the formulations as shown in Table 6 were prepared, and the foam richness, rinsing effect and skin irritation thereof are shown, together with Comparative Examples, in Table 6. Examples having additives, etc., formulated therein are also shown.

TABLE 6
(Unit: wt. %)

| Component | Average molecular weight | Example 54 | Example 55 | Example 56 | Comparative Example 36 | Comparative Example 37 | Comparative Example 38 | Comparative Example 39 | Example 57 | Example 58 | Example 59 | Example 60 | Example 61 | Comparative Example 40 | Comparative Example 41 | Comparative Example 42 |
|---|---|---|---|---|---|---|---|---|---|---|---|---|---|---|---|---|
| Stearyltrimethyl ammonium chloride | 348 | 2.44 | — | — | — | — | — | — | — | — | — | — | — | — | — | — |
| Compound of the formula (III) ($R_7=12$, $X_3=Cl$) | 527 | — | 3.69 | — | — | 2.44 | — | — | — | — | — | — | — | — | — | — |
| Compound of the formula (II) ($R_5=18$, $R_6=1$, $m+n=4$, $X_2=Cl$) | 495 | — | — | 3.47 | 3.47 | — | 1.98 | 2.97 | 3.96 | 4.95 | 5.94 | 6.93 | 7.92 | 8.91 | 0.17 | 19.30 |
| POE nonylphenyl ether (EO = 10) | | — | — | — | 10 | 10 | 10 | 10 | 10 | 10 | 10 | 10 | 10 | 10 | 10 | 10 |
| Alkylglycoside (n = 12, x = 1) | 222 | 10 | 10 | 10 | — | — | — | — | — | — | — | — | — | — | — | — |
| Sodium laurate | 433 | — | — | — | — | — | — | — | — | — | — | — | — | — | — | — |
| Potassium myristoyl glutamate | 433 | 1.30 | 1.30 | 1.30 | 1.30 | — | 6.93 | 6.06 | 5.20 | 4.33 | 3.46 | 2.60 | 1.73 | 0.87 | 0.04 | 4.66 |
| Sodium lauryl sulfate | 288 | — | — | — | — | 0.86 | — | — | — | — | — | — | — | — | — | — |
| Water | | Balance | " | " | " | " | " | " | " | " | " | " | " | " | " | " |
| Cationic surfactant / Anionic surfactant (molar ratio) | | 7/3 | 7/3 | 7/3 | 7/3 | 7/3 | 2/8 | 3/7 | 4/6 | 5/5 | 6/4 | 7/3 | 8/2 | 9/1 | 6.5/3.5 | 6.5/3.5 |
| Rinsing effect | | | | | | | | | | | | | | | | |
| Smoothness | | ◎ | ◎ | ◎ | ◎ | × | △ | ○ | ◎ | ◎ | ◎ | ◎ | ◎ | ○ | × | ◎ |
| Luster | | ◎ | ◎ | ◎ | ◎ | × | × | △ | ○ | ◎ | ◎ | ◎ | ◎ | ○ | × | ◎ |
| Comb-out property | | ◎ | ◎ | ◎ | ◎ | × | × | ○ | ◎ | ◎ | ◎ | ◎ | ○ | △ | ○ | ◎ |
| Skin irritation (protein denaturation) | | ◎ | ◎ | ◎ | ◎ | × | ○ | ○ | ◎ | ◎ | ◎ | ◎ | ◎ | × | × | × |
| Richness | | ◎ | ◎ | ◎ | × | △ | ◎ | ◎ | ◎ | ◎ | ◎ | ◎ | ◎ | ◎ | ◎ | ◎ |

EXAMPLE 62

A shampoo having the following formulation was prepared (molar ratio of cationic surfactant/anionic surfactant=6/4) and evaluated by the same method as used in Examples 54 to 61.

| Components | % by weight |
|---|---|
| Alkylglycoside (n = 8, x = 1) | 15.0 |
| Polymer JR-400 (produced by Union Carbide Co.) | 0.2 |
| Behenyltrimethylammonium chloride (average MW = 404) | 2.42 |
| Sodium lauroyl methyl-$\beta$-alanine (average MW = 307) | 1.23 |
| Propylene glycol | 5.0 |
| Polyoxyethylene (average 40 mol) hardened castor oil derivative | 2.0 |
| Betaine N-lauryldimethylacetate | 5.0 |
| Colorant, perfume | q.s. |
| Deionized water | balance |

This shampoo was found to have an excellent rinsing effect, foam richness, and little skin irritation.

EXAMPLE 63

A body shampoo having the following formulation was prepared (molar ratio of cationic surfactant/anionic surfactant=7/3) and evaluated by the same method as used in Examples 54 to 62.

| Components | % by weight |
|---|---|
| Alkylglycoside (n = 10, x = 2) | 30.0 |
| Compound of the formula (II) [$R_5$ = 18, $R_6$ = 1, m + n = 2, average MW = 407, $X_2$ = Cl] | 2.85 |
| Sodium lauroylsarcosinate (average MW = 293) | 0.88 |
| Laurylimidazoline betaine | 10.0 |
| Dipropylene glycol | 8.0 |
| Aloe extract | 0.5 |
| Colorant, perfume | q.s. |
| Preservative, chelating agent | q.s. |
| Deionized water | balance |

This body shampoo was found to have an excellent rinsing effect, foam richness, and little skin irritation.

EXAMPLE 64

A body shampoo having the following formulation was prepared (molar ratio of cationic surfactant/anionic surfactant=7/3) and evaluated by the same method as used in Examples 54 to 63.

| Components | % by weight |
|---|---|
| Alkylglycoside (n = 12, x = 3) | 20.0 |
| Polycoat H | 2.0 |
| Coconut fatty acid diethanolamide | 5.0 |
| Compound of the formula (II) [$R_5$ = 18, $R_6$ = 1, m + n = 4, average MW = 495, $X_2$ = Cl] | 3.47 |
| Sodium laurylsarcosinate (average MW = 293) | 0.88 |
| Propylene glycol | 3.0 |
| Colorant, perfume | q.s. |
| Deionized water | balance |

This hair shampoo was found to have an excellent rinsing effect, foam richness, and little skin irritation.

EXAMPLE 65

A body shampoo having the following formulation was prepared (molar ratio of cationic surfactant/anionic surfactant=6/4) and evaluated by the same method as used in Examples 54 to 64.

| Components | % by weight |
|---|---|
| Sodium 2-undecyl-N,N,N-(hydroxyethyl-carboxymethyl)-2-imidazoline | 2.0 |
| Polycoat H | 1.0 |
| Coconut fatty acid diethanolamide | 0.5 |
| Compound of the formula (II) [$R_5$ = 20, $R_6$ = 1, m + n = 10, average MW = 787, $X_2$ = Cl] | 4.72 |
| Sodium lauroylsarcosinate (average MW = 293) | 1.17 |
| Alkylglycoside (n = 14, x = 2) | 10.0 |
| Dipropylene glycol | 1.0 |
| Colorant, perfume | q.s. |
| Deionized water | balance |

This body shampoo was found to have an excellent rinsing effect, foam richness, and little skin irritation.

EXAMPLE 66

A liquid detergent for clothing having the following formulation (molar ratio of cationic surfactant/anionic surfactant=5/5) was prepared and the softness of the clothing after washing was organoleptically evaluated.

| Components | % by weight |
|---|---|
| Alkylglycoside (n = 16, x = 1) | 30.0 |
| Compound of the formula (II) [$R_5$ = 18, $R_6$ = 1, m + n = 4, average MW = 495, $X_2$ = Cl] | 4.95 |
| Sodium lauroyl methyl-$\beta$-alanine (average MW = 307) | 3.07 |
| Betaine lauryldimethylaminoacetate | 5.0 |
| Fluorescent dye | 0.2 |
| Ethanol | 8.0 |
| Colorant, perfume | q.s. |
| Sodium hydroxide | q.s. |
| Deionized water | balance |

As explained above, according to the present invention, a detergent composition having an excellent conditioning effect and low skin irritation can be provided.

We claim:

1. A detergent composition comprising, in an aqueous medium, (i) at least one quaternary ammonium cationic surfactant selected from the group consisting of (a) monoalkyl quaternary ammonium salt cationic surfactants having the formula (I):

wherein $R_1$ represents an alkyl or alkenyl having 12 to 22 carbon atoms, $R_2$, $R_3$, and $R_4$ independently represent methyl or ethyl, and $X_1$ represents a halogen atom or a methylsulfate residue, (b) ethylene oxide addition quaternary ammonium salt cationic surfactants having the formula (II):

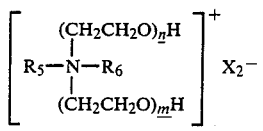

wherein R$_5$ represents an alkyl having 16 to 22 carbon atoms, R$_6$ represents methyl, ethyl, or an alkyl having 16 to 22 carbon atoms, X$_2$ represents a halogen atom or a methylsulfate or ethylsulfate residue, m and n are independently an integer of at least 1, provided that the sum of m and n is 2 to 30, and (c) imidazoline quaternary ammonium salt cationic surfactants having the formula (III):

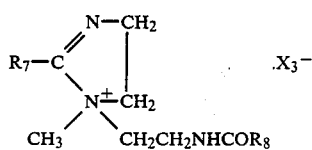

wherein R$_7$ and R$_8$ independently represent an alkyl or alkenyl having 12 to 22 carbon atoms, and X$_3$ represents a halogen atom or a methylsulfate or ethylsulfate residue;

(ii) at least one carboxylate anionic surfactant selected from the group consisting of:
N-acylsarcosinate anionic surfactants having the formula:

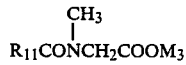

wherein R$_{11}$ represents an alkyl or alkenyl group having 8 to 18 carbon atoms and M$_3$ represents one or more of alkali metals, organic amines, and basic amino acids;
N-acylglutamates having the formula:

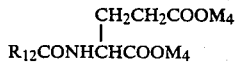

wherein R$_{12}$ represents an alkyl or alkenyl group having 8 to 18 carbon atoms and M$_4$ independently represents one or more of alkali metals, organic amines, and basic amino acids;
N-acyl-N-methyl-β-alanine salt anionic surfactants having the formula:

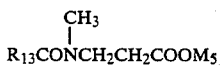

wherein R$_{13}$ represents an alkyl or alkenyl group having 8 to 18 carbon atoms and M$_5$ represents one or more of alkali metals, organic amines, and basic amino acids; and
N-acyl alanine salt anionic surfactant having the formula:

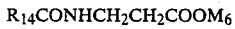

wherein R$_{14}$ represents an alkyl or alkenyl group having 8 to 18 carbon atoms and M$_6$ represents one or more of alkali metals, organic amines, and basic amino acids; and (iii) at least one amphoteric surfactant, the mole ratio of the components (i)/(ii) being within the range of from 4/6 to 8/2.

2. A detergent composition as claimed in claim 1, wherein said cationic surfactant (i) is selected from the group consisting of the monoalkyl quaternary ammonium salt cationic surfactants (a) having the formula (I).

3. A detergent composition as claimed in claim 1, wherein said cationic surfactant (i) is selected from the group consisting of the ethylene oxide addition quaternary ammonium salt cationic surfactants (b) having the formula (II).

4. A detergent composition as claimed in claim 1, wherein said cationic surfactant (i) is selected from the group consisting of the imidazoline quaternary ammonium salt cationic surfactants (c) having the formula (III).

5. A detergent composition as claimed in claim 1, wherein said carboxylate anionic surfactant (ii) is at least one N-acylsarcosinate anionic surfactant having the formula:

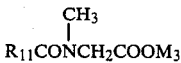

wherein R$_{11}$ represents an alkyl or alkenyl group having 8 to 18 carbon atoms and M$_3$ represents one or more of alkali metals, organic amines and basic amino acids.

6. A detergent composition as claimed in claim 1, wherein said carboxylate anionic surfactant (ii) is at least one N-acylglutamate having the formula:

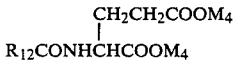

wherein R$_{12}$ represents an alkyl or alkenyl group having 8 to 18 carbon atoms and M$_4$ independently represents one or more of alkali metals, organic amines, and basic amino acids.

7. A detergent composition as claimed in claim 1, wherein said carboxylate anionic surfactant (ii) is at least one N-acyl-N-methyl-β-alanine salt anionic surfactant having the formula:

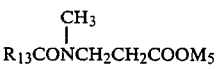

wherein R$_{13}$ represents an alkyl or alkenyl group having 8 to 18 carbon atoms and M$_5$ represents one or more of alkali metals, organic amines, and basic amino acids.

8. A detergent composition as claimed in claim 1, wherein said carboxylate anionic surfactant (ii) is at least one N-acyl alanine salt anionic surfactant having the formula:

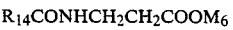

wherein R$_{14}$ represents an alkyl or alkenyl group having 8 to 18 carbon atoms and M$_6$ represents one or more of alkali metals, organic amines, and basic amino acids.

9. A detergent composition as claimed in claim 1, wherein the amount of the amphoteric surfactant (iii) is 0.1% to 20% by weight based on the total weight of the composition.

10. A detergent composition as claimed in claim 1, wherein the total amount of the components (i) and (ii) is 0.5% to 20% by weight, based on the total amount of the detergent composition.

11. A detergent composition as claimed in claim 1, wherein the mole ratio of the components (i)/(ii) is 5/5 to 7/3.

12. A detergent composition as claimed in claim 1 further comprising (iv) at least one nonionic surfactant.

13. A detergent composition as claimed in claim 12, wherein said nonionic surfactant (iv) is at least one nonionic surfactant having an HLB value of 4 to 20.

14. A detergent composition as claimed in claim 12, wherein said nonionic surfactant (iv) is at least one alkyl glycoside having the formula (IV):

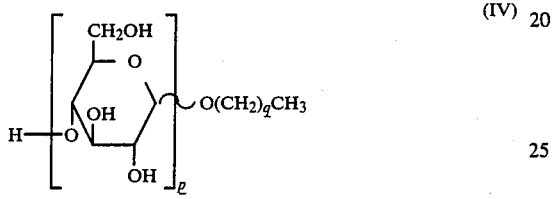

wherein p is an integer of 1 to 15 and q is an integer of 7 to 19.

15. A detergent composition as claimed in claim 12, wherein the amount of the nonionic surfactant (iv) is 5% to 70% by weight based on the total weight of the composition containing the components (i) to (iv).

16. A detergent composition comprising, in an aqueous medium, (i) at least one quaternary ammonium cationic surfactant selected from the group consisting of (a) monoalkyl quaternary ammonium salt cationic surfactants having the formula (I):

wherein $R_1$ represents an alkyl or alkenyl having 12 to 22 carbon atoms, $R_2$, $R_3$, and $R_4$ independently represent methyl or ethyl, and $X_1$ represents a halogen atom or a methylsulfate residue, (b) ethylene oxide addition quaternary ammonium salt cationic surfactants having the formula (II):

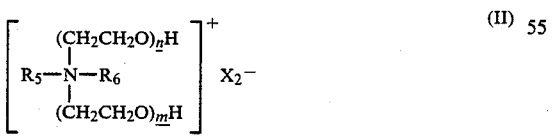

wherein $R_5$ represents an alkyl having 16 to 22 carbon atoms, $R_6$ represents methyl, ethyl, or an alkyl having 16 to 22 carbon atoms, $X_2$ represents a halogen atom or a methylsulfate or ethylsulfate residue, m and n are independently 0 or an integer of at least 1, provided that the sum of m and n is 1 to 30, and (c) imidazoline quaternary ammonium salt cationic surfactants having the formula (III):

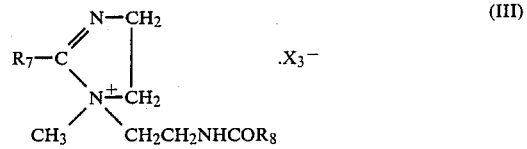

wherein $R_7$ and $R_8$ independently represent an alkyl or alkenyl having 12 to 22 carbon atoms, and $X_3$ represents a halogen atom or a methylsulfate or ethylsulfate residue;

(ii) at least one carboxylate anionic surfactant selected from the group consisting of:

N-acylsarcosinate anionic surfactants having the formula:

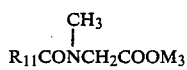

wherein $R_{11}$ represents an alkyl or alkenyl group having 8 to 18 carbon atoms and $M_3$ represents one or more of alkali metals, organic amines, and basic amino acids;

N-acyglutamates having the formula:

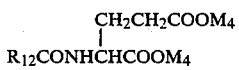

wherein $R_{12}$ represents an alkyl or alkenyl group having 8 to 18 carbon atoms and $M_4$ independently represents one or more of alkali metals, organic amines, and basic amino acids;

N-acyl-N-methyl-β-alanine salt anionic surfactants having the formula:

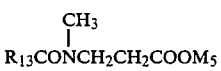

wherein $R_{13}$ represents an alkyl or alkenyl group having 8 to 18 carbon atoms and $M_5$ represents one or more of alkali metals, organic amines, and basic amino acids; and N-acyl alanine salt anionic surfactant having the formula:

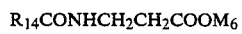

wherein $R_{14}$ represents an alkyl or alkenyl group having 8 to 18 carbon atoms and $M_6$ represents one or more of alkali metals, organic amines, and basic amino acids; and (iv) at least one nonionic surfactant, the mole ratio of the components (i)/(ii) being within the range from 4/6 to 8/2.

17. A detergent composition as claimed in claim 16, wherein said nonionic surfactant (iv) is at least one nonionic surfactant having an HLB value of 4 to 20.

18. A detergent composition as claimed in claim 16, wherein said nonionic surfactant (iv) is at least one alkyl glycoside having the formula (IV):

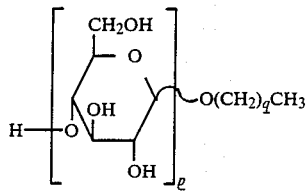 (IV)

wherein p is an integer of 1 to 15 and q is an integer of 7 to 19.

19. A detergent composition as claimed in claim 16, wherein the amount of the nonionic surfactant (iv) is 5% to 70% by weight based on the total weight of the composition containing the components (i), (ii), and (iv).

20. A detergent composition as claimed in claim 16, wherein said cationic surfactant (i) is selected from the group consisting of the ethylene oxide addition quaternary ammonium salt cationic surfactants (b) having the formula (II) and the imidazoline quaternary ammonium salt cationic surfactants (c) having the formula (III). organic amines, and basic amino acids.

21. A detergent composition as claimed in claim 16, wherein said carboxylate anionic surfactant (ii) is at least one N-acylsarcosinate anionic surfactant having the formula:

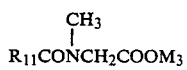

wherein $R_{11}$ represents an alkyl or alkenyl group having 8 to 18 carbon atoms and $M_3$ represents one or more of alkali metals, organic amines and basic amino acids.

22. A detergent composition as claimed in claim 16, wherein said carboxylate anionic surfactant (ii) is at least one N-acylglutamate having the formula:

wherein $R_{12}$ represents an alkyl or alkenyl group having 8 to 18 carbon atoms and $M_4$ independently represents one or more of alkali metals, organic amines, and basic amino acids.

23. A detergent composition as claimed in claim 16, wherein said carboxylate anionic surfactant (ii) is at least one N-acyl-methyl-β-alanine salt anionic surfactant having the formula:

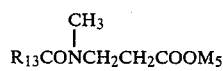

wherein $R_{13}$ represents an alkyl or alkenyl group having 8 to 18 carbon atoms and $M_5$ represents one or more of alkali metals, organic amines, and basic amino acids.

24. A detergent composition as claimed in claim 16, wherein said carboxylate anionic surfactant (ii) is at least one N-acyl alanine salt anionic surfactant having the formula:

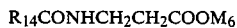

wherein $R_{14}$ represents an alkyl or alkenyl group having 8 to 18 carbon atoms and $M_6$ represents one or more of alkali metals, organic amines, and basic amine acids.

* * * * *

UNITED STATES PATENT AND TRADEMARK OFFICE
CERTIFICATE OF CORRECTION

PATENT NO. : 4,919,846

DATED : April 24, 1990

INVENTOR(S) : Yasunari Nakama, et al

It is certified that error appears in the above-identified patent and that said Letters Patent is hereby corrected as shown below:

Col. 29, line 35          After "$CONCH_2$" insert --$CH_2$--

Col. 33, line 27          Delete "organic amines, and basic amino acids."

Signed and Sealed this

Nineteenth Day of May, 1992

*Attest:*

DOUGLAS B. COMER

*Attesting Officer*         *Acting Commissioner of Patents and Trademarks*